US007935331B2

(12) United States Patent
Lin

(10) Patent No.: US 7,935,331 B2
(45) Date of Patent: May 3, 2011

(54) VANILLIN POLYMERS FOR USE IN DARKENING THE SKIN

(75) Inventor: Connie Baozhen Lin, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 1536 days.

(21) Appl. No.: 10/735,540

(22) Filed: Dec. 12, 2003

(65) Prior Publication Data

US 2005/0129633 A1    Jun. 16, 2005

(51) Int. Cl.
*A61K 8/30* (2006.01)
(52) U.S. Cl. ........................... 424/59; 424/60
(58) Field of Classification Search .............. 424/59
See application file for complete search history.

(56) References Cited

U.S. PATENT DOCUMENTS

| 2,553,146 | A |   | 5/1951  | Pearl |
| 4,230,817 | A | * | 10/1980 | Charbonneau ............ 528/206 |
| 4,690,825 | A |   | 9/1987  | Won |
| 4,714,609 | A | * | 12/1987 | Carden ...................... 424/59 |
| 5,013,497 | A |   | 5/1991  | Yiournas et al. |
| 5,145,675 | A |   | 9/1992  | Won |
| 5,216,116 | A |   | 6/1993  | Pawelek et al. |
| 5,218,079 | A |   | 6/1993  | Pawelek et al. |
| 5,225,435 | A |   | 7/1993  | Pawelek et al. |
| 5,227,459 | A |   | 7/1993  | Pawelek et al. |
| 5,247,055 | A |   | 9/1993  | Stenger-Smith et al. |
| 5,260,065 | A |   | 11/1993 | Mathur et al. |
| 5,384,116 | A |   | 1/1995  | Pawelek et al. |
| 5,618,519 | A |   | 4/1997  | Pawelek et al. |
| 5,744,125 | A | * | 4/1998  | Pawelek et al. ............ 424/59 |
| 6,284,234 | B1|   | 9/2001  | Niemiec et al. |

OTHER PUBLICATIONS

Wenninger, J., McEwen, G. Pepe, R.C., International Cosmetic Ingredient Dictionary and Handbook, Ninth Edition, The Cosmetic, Toiletry and Fragrance Association, 2002, pp. 2892, 2922-2923, 2926-2928, 2930-2936, 2962-2971, 2979-2984.
International Search Report dated Apr. 27, 2005, for corresponding PCT application PCT/US2004/041716.

* cited by examiner

*Primary Examiner* — Jake M. Vu

(57) ABSTRACT

The present invention features polymers containing vanillin monomers and/or o-vanillin monomers and the use thereof in darkening the skin.

18 Claims, No Drawings

VANILLIN POLYMERS FOR USE IN DARKENING THE SKIN

FIELD OF THE INVENTION

The present invention relates to polymers containing monomeric units of vanillin and the use thereof to darken the skin.

BACKGROUND OF THE INVENTION

The darkening of skin color is a concern for many individuals. Most people obtain darker skin through exposure to UV light (e.g., suntanning or UV lamps). Production of melanin and the type of melanin when stimulated by UV are genetically determined. UV exposure, however, results in accelerated skin aging and increased incidence of skin cancer. The ability to generate a tanned appearance without incurring photodamage, thus, is important to many individuals. Accordingly, alternative methods for "sunless tanning" have evolved.

One method is the use of products containing dihydroxy acetone (DHA). Some of these products, however, produce color that is too orange and unnatural to the user. Moreover, the DHA-produced skin color only minimally protects the user from UV irradiation. Products containing beta-carotene, cantaxanthin and lycopene have also been used to darken the skin. These products, however, have no effect at all on melanogenesis and usually result in unnatural and uneven distributed skin color by saturating and staining the fat layers just below the skin. In addition, these products do not provide any sun-protection as compared to naturally tanned skin.

Melanotan and MelanX are synthetic hormone drugs that mimic the action of melanocyte-stimulating hormone (MSH) and are used to darken the skin only when administered by injection, not orally or topically. Psoralens, on the other hand, work by making the skin hypersensitive to the sun and therefore melanin production is accelerated. They do not make the skin darker without exposure to UV, and that exposure must be carefully regulated to minimize the serious risk for skin cancer. Psoralens in conjunction with medical grade UV lamps are an accepted treatment for people afflicted with vitiligo and psoriasis, but are not recommended for patients with fair skins.

Thus, a product is desired that would enhance the body's natural pigment content, resulting in a desired skin color and enhanced photo-protection without the need of UV exposure.

SUMMARY OF THE INVENTION

In one aspect, the present invention features a method of darkening the skin by applying to the skin a polymer containing vanillin monomers and/or o-vanillin monomers.

In another aspect, the present invention features a polymer containing (i) vanillin monomers and/or o-vanillin monomers and (ii) monomers selected from the group consisting of 3-aminotyrosine, dihydroxy acetone, 3,4-dihydroxybenzoic acid, 3-amino, 4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol, p-aminobenzoic acid, and mixtures thereof. In a further aspect, the present invention features a composition containing the above polymer and cosmetically-acceptable topical carrier and applying to said skin such composition.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., %(W/W)).

Definitions

What is meant by "darkening the skin or hair" is darkening the appearance of the skin or hair, including, but not limited to, darkening the skin to either achieve a "sun tan" effect or to cover the light areas of the skin (e.g., as a result of a scar or a disease such as vitiligo) or darkening natural hair color or restoring discolored hair due to aging (e.g., gray or white hair) or external aggressions (e.g., excess exposure to sun or chlorine).

What is meant by a "product" is a product in finished packaged form. In one embodiment, the package is a container such as a plastic, metal or glass tube or jar containing the composition. The product may further contain additional packaging such as a plastic or cardboard box for storing such container. In one embodiment, the product contains instructions directing the user to apply the composition to the skin or hair to darken the skin (e.g., to tan the skin), even skin tone (e.g., to darken light areas of the skin or to treat or prevent mottled hyperpigmentation), or darken the hair (e.g., to darken light brown, blonde, gray or white hairs). Such instructions may be printed on the container, label insert, or on any additional packaging.

What is meant by "promoting" is promoting, advertising, or marketing. Examples of promoting include, but are not limited to, written, visual, or-verbal statements made on the product or in stores, magazines, newspaper, radio, television, internet, and the like. Examples of such statements include, but are not limited to, "evens skin tone," "darkens the skin," "evens hair color," "darkens the hair," "restore the original hair color," "treats and/or prevents gray hair," "prevents, reduces, and/or treats mottled hyperpigmentation," "tans the skin," or "sunless tan."

As used herein, "topically applying" means directly laying on or spreading on outer skin, scalp, or hair, e.g., by use of the hands or an applicator such as a wipe, roller, or spray.

As used herein, "cosmetically-acceptable" means that the ingredients which the term describes are suitable for use in contact with tissues (e.g., the skin or hair) without undue toxicity, incompatibility, instability, irritation, allergic response, and the like.

As used herein, "safe and effective amount" means an amount of the polymer or of the composition sufficient to induce a darkening of the skin or hair, but low enough to avoid serious side effects. The safe and effective amount of the compounds or composition will vary with the area being treated, the age and skin type of the end user, the duration and nature of the treatment, the specific extract, ingredient, or composition employed, the particular cosmetically-acceptable carrier utilized, and like factors.

Vanillin Polymers

The vanillin polymers of the present invention include vanillin monomer and/or o-vanillin monomers. In one embodiment, the polymer further includes one or more of the following monomeric units: 3-aminotyrosine, dihydroxy acetone, 3,4-dihydroxybenzoic acid, 3-amino, 4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol, and p-aminobenzoic acid. In one embodiment, the polymer has an average molecular weight of from about 10 kd to about 50 kd, such as from about 15 kd to about 40 kd.

The vanillin polymers of the present invention are made from vanillin and/or o-vanillin monomers. These polymers can be manufactured by one of ordinbary skill in the art, such as set forth in U.S. Pat. No. 5,744,125 (e.g., where the processes are modified to use vanillin and/or o-vanillin as a pre-cursor monomer). Examples of such synthesis is set forth below in Example 1.

In one embodiment, the vanillin polymer also includes one or more of the following moieties: fatty acids such as linoleic acid, 9,10-dihydroxystearic acid, and linolenic acid; steroids such as cholesterol; and carbazole alkaloids such as dihydroxycarbazole. Such compounds can be included in the polymerization reactions.

Pigment

In one embodiment, the composition of the present invention further contains at least one pigment. What is meant by a "pigment" is a compound(s) that can be taken up by epidermal cells, resulting in visually darker look to the skin or hair. Examples of such pigments include, but not limiting to, other melanin and melanin derivatives (e.g., both melanin polymers and lower molecular weight water-soluble melanin derivatives); extracts from natural sources containing pigments (e.g., brown pigments from plants from the *Hedychium* genus, *Rhubarb* genus, or *Bearberry* genus or yellow, orange and red pigments, from plants containing carotenoids or canthaxanthins); or synthetic chemicals such as compounds containing copper (e.g., copper salts such as copper PCA or $CuCl_2$) or synthetic carotenoids or canthaxantins. Examples of synthetic melanin derivatives are disclosed in U.S. Pat. Nos. 5,618,519, 5,384,116, and 5,227,459. Examples of soluble melanin derivatives are disclosed in U.S. Pat. Nos. 5,744,125, 5,225,435, 5,218,079, and 5,216,116. Examples of commercially available soluble melanin derivatives include Melasyn-100™ from San-mar laboratories, Inc. (Elmsford, N.Y.) and MelanZe™ from Zylepsis (Ashford, Kent, United Kingdom). The amount of pigment(s) present in the composition will depend on the type of pigment(s) used. The pigments typically will be present in the composition in an amount from about 0.001% to about 20% by weight, in particular in an amount from about 0.005% to about 5% by weight.

Dihydroxy Acetone and Lawsone

In one embodiment, the composition of the present invention further contains dihydroxyacetone and/or lawsone. These agents will typically be present in the composition in an amount from about 0.001% to about 10% by weight, in particular in an amount from about 1% to about 7% by weight. In one embodiment, the composition of the present invention contains both dihydroxyacetone and at least one pigment.

Peptides

In one embodiment, the composition of the present invention further contains a peptide of the Formula I

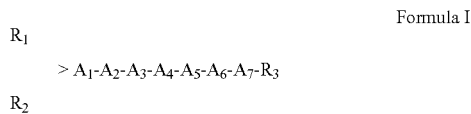

Formula I wherein:
- $A_1$ is Ser or 2,3-diaP, or is absent;
- $A_2$ is Val, Leu, Ile, or Cha;
- $A_3$ is Val, Leu, Ile, or Cha;
- $A_4$ is Gly or Ala;
- $A_5$ is Lys, Arg, or Har;
- $A_6$ is Val, Leu, Ile, or Cha, or is absent;
- $A_7$ is Asp or Glu, or is absent; provided, $A_7$ is absent if $A_6$ is absent;
- each $R_1$ and $R_2$, independently, is H, $C_{1-12}$ alkyl, $C_{7-10}$ phenylalkyl, or $C(=O)E_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is $C(=O)E_1$, the other must be H; and
- $R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;

or a cosmetically acceptable salt thereof.

In one embodiment, $R_1$ and $R_2$, which are bound to the N-terminus of the peptide, are both H. In another embodiment, $R_1$ is H and $R_2$ is $C(=O)E_1$ (e.g., palmitoyl, oleatoyl, or stearatoyl).

Examples of peptides of the present invention include, but are not limited to, to $H_2$-Leu-Ile-Gly-Arg-$NH_2$ (SEQ ID NO:1), $H_2$-Leu-Ile-Gly-Arg-Leu-$NH_2$ (SEQ ID NO:2), $H_2$-Leu-Ile-Gly-Lys-$NH_2$ (Peptide 3, SEQ ID NO:3), $H_2$-Ser-Leu-Ile-Gly-Lys-$NH_2$ (Peptide 4, SEQ ID NO:4), $H_2$-Leu-Ile-Gly-Arg-OH (SEQ ID NO:5), $H_2$-Leu-Ile-Gly-Arg-Leu-OH (SEQ ID NO:6), $H_2$-Leu-Ile-Gly-Lys-OH (SEQ ID NO:7), $H_2$-Ser-Leu-Ile-Gly-Lys-OH (SEQ ID NO:8), Palmitoyl-Leu-Ile-Gly-Arg-$NH_2$ (SEQ ID NO:9), Palmitoyl-Leu-Ile-Gly-Arg-Leu-$NH_2$(SEQ ID NO:10), Palmitoyl-Leu-Ile-Gly-Lys-$NH_2$ (SEQ ID NO:11), Palmitoyl-Ser-Leu-Ile-Gly-Lys-$NH_2$ (SEQ ID NO:12), Palmitoyl-Leu-Ile-Gly-Arg-OH (SEQ ID NO:13), Palmitoyl-Leu-Ile-Gly-Arg-Leu-OH (SEQ ID NO:14), Palmitoyl-Leu-Ile-Gly-Lys-OH (SEQ ID NO:15), Palmitoyl-Ser-Leu-Ile-Gly-Lys-OH (SEQ ID NO:16), Stearatoyl-Leu-Ile-Gly-Arg-$NH_2$ (SEQ ID NO:17), Stearatoyl-Leu-Ile-Gly-Arg-Leu-$NH_2$(SEQ ID NO:18), Stearatoyl-Leu-Ile-Gly-Lys-$NH_2$ (SEQ ID NO:19), Stearatoyl-Ser-Leu-Ile-Gly-Lys-$NH_2$ (SEQ ID NO:20), Stearatoyl-Leu-Ile-Gly-Arg-OH (SEQ ID NO:21), Stearatoyl-Leu-Ile-Gly-Arg-Leu-OH (SEQ ID NO:22), Stearatoyl-Leu-Ile-Gly-Lys-OH (SEQ ID NO:23), Stearatoyl-Ser-Leu-Ile-Gly-Lys-OH (SEQ ID NO:24), $H_2$-Ser-Leu-Ile-Gly-Arg-Leu-$NH_2$ (SEQ. ID. No.25), $H_2$-Ser-Leu-Ile-Gly-Arg-Leu-OH (SEQ. ID. No.26), Palmitoyl-Ser-Leu-Ile-Gly-Arg-Leu-$NH_2$ (SEQ. ID. No.27), Palmitoyl-Ser-Leu-Ile-Gly-Arg-Leu-OH (SEQ. ID. No.28), Stearatoyl-Ser-Leu-Ile-Gly-Arg-Leu-$NH_2$ (SEQ. ID. No.29), and Stearatoyl-Ser-Leu-Ile-Gly-Arg-Leu-OH (SEQ. ID. No.30), or a cosmetically-acceptable salt thereof.

The symbol $A_1$, $A_2$, or the like used herein (e.g., in FIG. 1) stands for the residue of an alpha-amino acid. Such symbols represent the general structure, —NH—CH(X)—CO— or =N—CH(X)—CO— when it is at the N-terminus or —NH—CH(X)—CO— when it is not at the N-terminus, where X denotes the side chain (or identifying group) of the alpha-amino acid, e.g., X is —CH(CH$_3$)$_2$ for Val. Note that the N-terminus is at the left and the C-terminus at the right in accordance with the conventional representation of a polypeptide chain. $R_1$ and $R_2$ are both bound to the free nitrogen atom N-terminal amino acid (e.g., $A_1$ or $A_2$) and the $R_3$ is bound to the free carboxy group of the C-terminal amino acid (e.g., $A_5$, $A_6$, or $A_7$).

"Cha" herein refers to cyclohexylalanine, "2,3-diaP" refers to 2,3-diaminoproprionic acid, and "Har" refers to homoarginine. Furthermore, where the amino acid residue is optically active, it is the L-form configuration that is intended unless the D-form is expressly designated. An alkyl group, if not specified, contains 1-12 carbon atoms.

The peptide of the invention can be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or pamoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition will depend on the peptide used. The peptide typically will be present in the composition in an amount from about 0.001% to about 10% by weight, in particular in an amount from about 0.005% to about 5% by weight.

The method for synthesizing peptides of the present invention are well documented and are within the ability of a person of ordinary skill in the art.

Topical Compositions

The topical compositions useful in the present invention involve formulations suitable for topical application to the skin or hair. In one embodiment, the composition contains a safe and effective amount of (i) at least one vanillin polymer and (ii) a cosmetically-acceptable topical carrier. In one embodiment, the cosmetically-acceptable topical carrier is from about 50% to abut 99.99%, by weight, of the composition (e.g., from about 80% to about 99%, by weight, of the composition.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, nail lacquers, wound dressing and adhesive bandages, hydrogels, film-forming products, facial masks and skin masks, films and make-up such as foundations, mascaras, and lipsticks. These product types may contain several types of cosmetically-acceptable topical carriers including, but not limited to solutions, suspensions, emulsions such as microemulsions and nanoemulsions, gels, solids and liposomes. The following are non-limitative examples of such carriers. Other carriers can be formulated by those of ordinary skill in the art.

The topical compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, and mixtures thereof.

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Pepe, Wenninger and McEwen, pp. 2930-36 (The Cosmetic, Toiletry, and Fragrance Assoc., Washington, D.C., 9$^{th}$ Edition, 2002) (hereinafter "ICI Handbook").

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The topical compositions of the present invention may also be anhydrous compositions containing no water but organic and/or silicone solvents, oils, lipids and waxes.

Yet another type of product that may be formulated from a solution is an ointment. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 2979-84.

The topical compositions useful in the present invention formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp. 2962-71.

Lotions and creams can be formulated as emulsions. Typically such lotions contain from 0.5% to about 5% of an emulsifier(s). Such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. In one embodiment, the vanillin polymer, dihydroxyacetone, lawsone, pigment, and/or peptide are contained within the liposome. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water. Epidermal lipids of suitable composition for forming liposomes may be substituted for the phospholipid. The liposome preparation may then incorporated into one of the above carriers (e.g., a gel or an oil-in-water emulsion) in order to produce the liposomal formulation.

In one-embodiment, the liposome is non-ionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome contains glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical composition in an amount, based upon the total volume of the composition, of from about 5 mg/ml to about 100 mg/ml such as from about 10 mg/ml to about 50 mg/ml. Methods of preparing liposomes are well known in the art, such as those disclosed in U.S. Pat. Nos. 5,013,497 and 5,260,065.

Micelle formulations are also useful compositions of the present inventions. Such micelle compositions are disclosed in the U.S. Pat. No. 6,284,234.

Other encapsulation technologies are also useful in the compositions of the present invention, such porous beads such as those described in U.S. Pat. Nos. 4,690,825 and 5,145,675.

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further contains another cosmetically active agent in addition to the vanillin polymer. What is meant by a "cosmetically active agent" is a compound (e.g., a synthetic compound or a compound isolated from a natural source) that has a cosmetic or therapeutic effect on the skin, hair, or nails, including, but not limiting to, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides, amino acids such as proline, vitamins, lactobionic acid, acetyl-coenzyme A, niacin, riboflavin, thiamin, ribose, electron transporters such as NADH and FADH2, and other botanical extracts such as aloe vera, and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Other Materials

Various other materials may also be present in the compositions useful in the subject invention. These include humectants, pH adjusters, chelating agents (e.g., EDTA), and preservatives (e.g., parabens). Examples of such agents are listed in pp. 2922-23, 2926-28, and 2892 of the ICI Handbook. In addition, the topical compositions useful herein can contain conventional cosmetic adjuvants, such as dyes, opacifiers (e.g., titanium dioxide), and fragrances.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

The composition and formulations containing such compositions of the present invention may be prepared using methodology that is well known by an artisan of ordinary skill.

EXAMPLE 1

Synthesis of Vanillin Polymers

Various polymers of the present invention are recited in Table 1. The polymers were synthesized either by protocol A ("Pr" A) for polymers not containing Linoleic Acid and protocol B ("Pr" B) for polymers containing linoleic acid, with the exception of Polymer 68, as set forth below. The monomers used, their respective mass and ratios, and the resulting mass of the polymer ("poly mass") and resulting yield of the synthesis ("Y %") are indicated in Table 1.

Protocol A. The following is a description of the synthesis of Polymer 61 pursuant to this protocol A. Other polymers of Table 1, was are indicated as being synthesized by protocol A, were synthesized in a similar manner. A 500-ml, round-bottom flask equipped with a magnetic stir bar was charged with aloin (4.67 g) and vanillin (2.33 g). Concentrated ammonium hydroxide (15M, 25 ml) was then added and stirring was initiated. After 5 min, copper sulfate pentahydrate (66 mg) was added, followed by water (40 ml). A deep red-brown color resulted and all the material appeared to be in solution. Hydrogen peroxide (7 mL, 30 wt %) was added drop wise over 2 min. After 10 min the reaction had heated to approximately 50 C, then cooled to a ambient temperature over 1 h, and was stirred vigorously for 14 h. The mixture was poured into stirred isopropyl alcohol (100 mL) in a 500-mL Erlenmeyer flask and the reaction flask was rinsed with an additional 70 mL isopropyl alcohol. The mixture was stirred for 10 min and a dark precipitate formed. The mixture was suction-filtered through paper (Whatman 1, 55 mm) to give a sticky brown solid. This material was transferred to a 300-mL beaker and isopropyl alcohol (150 mL) was added. The mixture was slurred and then suction-filtered again through paper to give a brown solid.

Protocol B. The following is a description of the synthesis of Polymer 4 pursuant to this protocol B. Other polymers of Table 1, was are indicated as being synthesized by protocol A, were synthesized in a similar manner. A 500-ml, round-bottom flask equipped with a magnetic stir bar was charged with aloin (4.2 g), vanillin (1.4 g), and linoleic acid (1.4 g). Concentrated ammonium hydroxide (15M, 25 ml) was then added and stirring was initiated. After 5 min, copper sulfate pentahydrate (66 mg) was added, followed by water (40 ml). A deep brown color resulted and all the material appeared to be in solution. Hydrogen peroxide (7 mL, 30 wt %) was added drop wise over 2 min. After 10 min the reaction had heated to approximately 50 C, then cooled to a ambient temperature over 1 h, and was stirred vigorously for 16 h. The mixture was poured into stirred isopropyl alcohol (100 mL) in a 500-mL Erlenmeyer flask and the reaction flask was rinsed with an additional 70 mL isopropyl alcohol. The mixture was stirred for 10 min, and then allowed to stand for 1 h. A dark oil colleted on the bottom of the flask. The supernatant was carefully decanted and replaced with 150 ml of isopropyl alcohol. The mixture was brought to reflux with mixing. The oil precipitate gradually began to harden and form a solid, which could be scraped from the bottom of the flask. After cooling, the mixture was suction-filtered through sintered glass to give a red-black solid.

Protocol C. The following is a description of the synthesis of Polymer 68. A 500-ml round-bottom flask equipped with a magnetic stir bar was charged with aloin (4.67 g), and L-DOPA (3,4-dihydroxyphenylalanine, 2.33 g), followed by concentrated ammonium hydroxide (15 M, 25 ml). The mixture was stirred and a deep brown color resulted. After 5 min, copper sulfate pentahydrate (66 mg) was added, followed by water (20 ml). Ammonium persulfate (21 g) was then added in 1.5-g portions spaced 10 min apart (total time of addition was 130 min). During this time, the reaction sustained a temperature of approximately 50° C. The mixture was stirred for 24 h, and then poured into 500 ml of water. While stirring, 500 ml of isopropyl alcohol was cautiously added and a light brown precipitate formed which did not settle upon prolonged standing. The mixture was centrifuged in 2×40-g portions at 800 rpm for 10 min, with the supernatant being removed after each run and replaced with fresh isopropyl alcohol suspension, to give a brown pellet. This was suspended in acetone (100 ml) and filtered to give a brown solid (4.62 g, 66% recovery).

TABLE 1

| POLYMER | MONOMER 1 | MONO 1 MASS (G) | MONOMER(S) 2 | MONO 2 MASS (G) | RATIO | PR | POLYMASS | Y(%) |
|---|---|---|---|---|---|---|---|---|
| 1 | Aloin | 2.8 | Vanillin/Linoleic Acid | 4.2 | 2:2:1 | B[1] | 2.98 | 43 |
| 2 | Aloin | 4.2 | Vanillin/Linoleic Acid | 2.8 | 3:1:1 | B[2] | 3.73 | 53 |
| 3 | Aloin | 2.8 | Vanillin/Linoleic Acid | 4.2 | 2:2:1 | B[3] | 3.01 | 43 |
| 4 | Aloin | 4.2 | Vanillin/Linoleic Acid | 2.8 | 3:1:1 | B | 3.9 | 56 |
| 5 | Aloin | 2.8 | Vanillin/L-DOPA | 4.2 | 2:2:1 | A | 4.46 | 64 |
| 6 | Aloin | 2.8 | Vanillin/L-DOPA | 4.2 | 2:2:1 | A[2] | 5.32 | 76 |
| 7 | Aloin | 4.2 | Vanillin/L-DOPA | 2.8 | 3:1:1 | A | 5.12 | 73 |
| 8 | Aloin | 4.2 | Vanillin/L-DOPA | 2.8 | 3:1:1 | A[2] | 5.6 | 80 |
| 9 | Aloin | 3.5 | Vanillin/Linoleic Acid | 3.5 | 3:2:1 | B | 3.76 | 54 |
| 10 | Aloin | 3.5 | Vanillin/Linoleic Acid | 3.5 | 3:2:1 | B[2] | 2.83 | 40 |
| 11 | Aloin | 3.5 | Vanillin/L-DOPA | 3.5 | 3:2:1 | A | 4.76 | 68 |
| 12 | Aloin | 3.5 | Vanillin/L-DOPA | 3.5 | 3:2:1 | A[2] | 4.62 | 66 |
| 13 | Vanillin | 1 | N/A | 0 | N/A | A | 0.21 | 21 |
| 14 | Vanillin | 1 | N/A | 0 | N/A | A[2] | 0.54 | 54 |
| 15 | Aloin | 3.5 | Vanillin | 3.5 | 1:1 | A[2] | 3.67 | 52 |
| 16 | Aloin | 3.67 | Vanillin | 3.33 | 1.1:1 | A[2] | 4.1 | 59 |
| 17 | Aloin | 3.82 | Vanillin | 3.18 | 1.2:1 | A[2] | 3.7 | 53 |
| 18 | Aloin | 3.96 | Vanillin | 3.04 | 1.3:1 | A[2] | 3.6 | 51 |
| 19 | Aloin | 4.08 | Vanillin | 2.92 | 1.4:1 | A[2] | 3.5 | 50 |
| 20 | Aloin | 3.5 | Vanillin | 3.5 | 1:1 | A | 3.84 | 55 |
| 21 | Aloin | 3.67 | Vanillin | 3.33 | 1.1:1 | A | 4.07 | 58 |
| 22 | Aloin | 3.82 | Vanillin | 3.18 | 1.2:1 | A | 3.89 | 56 |
| 23 | Aloin | 3.96 | Vanillin | 3.04 | 1.3:1 | A | 5.39 | 77 |
| 24 | Aloin | 4.08 | Vanillin | 2.92 | 1.4:1 | A | 4.28 | 61 |
| 25 | Aloin | 4.2 | Vanillin | 2.8 | 1.5:1 | A[2] | 4.03 | 58 |

TABLE 1-continued

| POLYMER | MONOMER 1 | MONO 1 MASS (G) | MONOMER(S) 2 | MONO 2 MASS (G) | RATIO | PR | POLYMASS | Y(%) |
|---|---|---|---|---|---|---|---|---|
| 26 | Aloin | 4.31 | Vanillin | 2.69 | 1.6:1 | $A^2$ | 3.77 | 54 |
| 27 | Aloin | 4.41 | Vanillin | 2.59 | 1.7:1 | $A^2$ | 3.62 | 52 |
| 28 | Aloin | 4.5 | Vanillin | 2.5 | 1.8:1 | $A^2$ | 3.82 | 55 |
| 29 | Aloin | 4.59 | Vanillin | 2.41 | 1.9:1 | $A^2$ | 4.08 | 58 |
| 30 | Aloin | 4.2 | Vanillin | 2.8 | 1.5:1 | A | 3.90 | 56 |
| 31 | Aloin | 4.31 | Vanillin | 2.69 | 1.6:1 | A | 4.04 | 58 |
| 32 | Aloin | 4.41 | Vanillin | 2.59 | 1.7:1 | A | 3.77 | 54 |
| 33 | Aloin | 4.5 | Vanillin | 2.5 | 1.8:1 | A | 4.87 | 70 |
| 34 | Aloin | 4.59 | Vanillin | 2.41 | 1.9:1 | A | 4.20 | 60 |
| 35 | Aloin | 2.96 | Vanillin/L-DOPA | 4.04 | 2.2:2:1 | A | 4.26 | 61 |
| 36 | Aloin | 3.11 | Vanillin/L-DOPA | 3.89 | 2.4:2:1 | A | 4.62 | 66 |
| 37 | Aloin | 3.25 | Vanillin/L-DOPA | 3.75 | 2.6:2:1 | A | 4.65 | 66 |
| 38 | Aloin | 3.38 | Vanillin/L-DOPA | 3.62 | 2.8:2:1 | A | 4.38 | 63 |
| 39 | Aloin | 3.61 | Vanillin/L-DOPA | 3.39 | 3.2:2:1 | A | 4.66 | 67 |
| 40 | Aloin | 3.72 | Vanillin/L-DOPA | 3.28 | 3.4:2:1 | A | 4.92 | 70 |
| 41 | Aloin | 3.82 | Vanillin/L-DOPA | 3.18 | 3.6:2:1 | A | 5.05 | 72 |
| 42 | Aloin | 3.91 | Vanillin/L-DOPA | 3.09 | 3.8:2:1 | A | 4.96 | 71 |
| 43 | Aloin | 4 | Vanillin/L-DOPA | 3 | 4:2:1 | A | 5.01 | 72 |
| 44 | Aloin | 3.5 | Vanillin/L-DOPA | 3.5 | 3:2:1 | $A^4$ | 4.78 | 68 |
| 45 | Aloin | 3.5 | Vanillin/L-DOPA | 3.5 | 3:2:1 | $A^5$ | 4.41 | 63 |
| 46 | Aloin | 3.5 | Vanillin | 3.5 | 1:1 | $A^6$ | 3.36 | 48 |
| 47 | Aloin | 3.5 | Vanillin | 3.5 | 1:1 | $A^7$ | 4.16 | 59 |
| 48 | Aloin | 3.5 | Vanillin | 3.5 | 1:1 | $A^8$ | 4.03 | 58 |
| 49 | Aloin | 3.5 | Vanillin | 3.5 | 1:1 | $A^9$ | 3.89 | 56 |
| 50 | Aloin | 3.5 | Vanillin | 3.5 | 1:1 | $A^{10}$ | 3.83 | 55 |
| 51 | Aloin | 3.5 | Vanillin | 3.5 | 1:1 | $A^{11}$ | 4.06 | 58 |
| 52 | Aloin | 3.33 | Vanillin | 3.67 | 1:1.1 | A | 2.91 | 42 |
| 53 | Aloin | 3.18 | Vanillin | 3.82 | 1:1.2 | A | 2.48 | 35 |
| 54 | Aloin | 3.04 | Vanillin | 3.96 | 1:1.3 | A | 2.22 | 32 |
| 55 | Aloin | 2.92 | Vanillin | 4.08 | 1:1.4 | A | 2.18 | 31 |
| 56 | Aloin | 2.8 | Vanillin | 4.2 | 1:1.5 | A | 2.4 | 34 |
| 57 | Aloin | 2.69 | Vanillin | 4.31 | 1:1.6 | A | 2.03 | 29 |
| 58 | Aloin | 2.59 | Vanillin | 4.41 | 1:1.7 | A | 1.71 | 24 |
| 59 | Aloin | 2.5 | Vanillin | 4.50 | 1:1.8 | A | 2.26 | 32 |
| 60 | Aloin | 2.41 | Vanillin | 4.59 | 1:1.9 | A | 2.17 | 31 |
| 61 | Aloin | 4.67 | Vanillin | 2.33 | 2:1 | A | 3.25 | 46 |
| 62 | Aloin | 4.67 | o-Vanillin | 2.33 | 2:1 | A | 5.63 | 77 |
| 63 | Aloin | 4.67 | Vanillin | 2.33 | 2:1 | B | 5.84 | 83 |
| 64 | Aloin | 2.33 | Vanillin | 4.67 | 1:2 | A | 3.25 | 46 |
| 65 | Aloin | 2.8 | Vanillin/ Linoleic Acid | 4.2 | 2:2:1 | B | 3.15 | 45 |
| 66 | Aloin | 4.67 | Vanillin | 2.33 | 2:1 | A | 3.25 | 46 |
| 67 | Aloin | 4.67 | Vanillin | 2.33 | 2:1 | $A^2$ | 3.69 | 53 |
| 68 | Aloin | 4.67 | L-DOPA | 2.33 | 2:1 | C | 4.62 | 66 |

Note 1: Three "equiv" $H_2O_2$ was added in 3-hours intervals.
Note 2: Two "equiv" $H_2O_2$ was added in 6-hours intervals.
Note 3: Two "equiv" $H_2O_2$ was added in 3-hours intervals.
Note 4: One and a half "equiv" $H_2O_2$ was added in 6-hours intervals.
Note 5: One and a half "equiv" $H_2O_2$ was added all in one portion.
Note 6: Two "equiv" $H_2O_2$ was added all in one portion.
Note 7: Two "equiv" $H_2O_2$ was added in 0.5-hours intervals.
Note 8: Two "equiv" $H_2O_2$ was added in 1-hour intervals.
Note 9: Two "equiv" $H_2O_2$ was added in 1.5-hours intervals.
Note 10: Two "equiv" $H_2O_2$ was added in 2-hours intervals.
Note 11: Two "equiv" $H_2O_2$ was added in 2.5-hours intervals.

EXAMPLE 2

Evaluation of Color, Solubility, Spectral Characteristics, and Tanning Properties of Synthesized Polymers The following is an evaluation of two polymer of the present invention (Compounds 59 and 11 from from Example 1) and a comparative polymer (Compound 68). The color of the polymers was evaluated in the form of solid powder or aqueous solution of polymers. The polymers were also tested for their solubility by visual evaluation of 1% W/W in deionized water. Table 2 defines the scale used in reporting the solubility.

TABLE 2

| SOLUBILITY | DESCRIPTION |
|---|---|
| High | Dissolve easily without sonication |
| Medium | Dissolve easily and completely with water bath sonication for 5-10 min |
| Medium-low | Do not dissolve completely with soincation |
| Low | Do not dissolve with soincation |

Spectral characteristics of the polymers were evaluated by dissolving polymer powders in deionized water at the concentration of 0.005% W/W. UV/Vis spectrum was determined in a spectrophotometer at 300 nm. As reported in U.S. Pat. No. 5,744,125, the spectrum of polymers suggests the potential UV protection, degree of polymerization, and molecular weight of polymers.

The polymers were also applied to human skin for skin deposition and tanning evaluation. Skin deposition was evaluated by applying to the lower arm compositions containing 1% by weight of the polymer in ethanol/propylene glycol vehicle (70/30, v/v %). The remaining polymer on skin was observed after first gently rubbing (10 times) the area under the running warm water. The remaining polymer on the skin was then subsequently evaluated by soap washing under the running warm water. The scale used for reporting skin deposition is defined in the Table 3.

TABLE 3

| SKIN DEPOSITION | DESCRIPTION |
| --- | --- |
| ++++ | visible color remained on skin both after water washing and after soap washing |
| ++ | visible color remained on skin after water washing but not after soap washing |
| 0 | No visible color remained after water washing |

The evaluation of the polymers are summarized in Table 4.

TABLE 4

| POLYMER | COLOR | SOLUBILITY | ABSORBANCE 300 NM | SKIN DEPOSITION |
| --- | --- | --- | --- | --- |
| 68 | Black-brown | Medium-high | 0.6 | ++++ |
| 59 | Dark-brown | Medium | 0.68 | ++++ |
| 11 | Black-brown | High | 0.63 | ++ |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of darkening the skin, said method comprising applying to said skin a polymer comprising (i) monomers selected from the group consisting of vanillin monomers, o-vanillin monomers, and mixtures thereof and (ii) monomers selected from the group consisting of 3-aminotyrosine, dihydroxy acetone, aloin, emodin, alizarin, tyrosine, dihydroxyphenylalanine, 4,5-dihydroxynaphthalene-2-sulfonic acid, 3-nitrotyrosine, 3-dimethylamino phenol, p-aminobenzoic acid, and mixtures thereof.

2. A method of claim 1, wherein said polymer comprises aloin monomers.

3. A method of claim 1, wherein said polymer comprises dihydroxyphenylalanine monomers.

4. A method of claim 1, wherein said polymer comprises aloin monomers and dihydroxyphenylalanine monomers.

5. A method of claim 1, wherein said polymer further comprises a moiety selected from the group consisting of linoleic acid, 9,10-dihydroxystearic acid, linolenic acid, cholesterol, dihydroxycarbazole, and mixtures thereof.

6. A method of claim 1, wherein said polymer has a molecular weight of from about 10 kd to about 50 kd.

7. A method of claim 2, wherein said polymer has a molecular weight of from about 10 kd to about 50 kd.

8. A method of claim 4, wherein said polymer has a molecular weight of from about 10 kd to about 50 kd.

9. A polymer comprising (i) monomers selected from the group consisting of vanillin monomers, o-vanillin monomers, and mixtures thereof and (ii) monomers selected from the group consisting of 3-aminotyrosine, dihydroxy acetone, aloin, emodin, alizarin, tyrosine, dihydroxyphenylalanine, 4,5-dihydroxynaphthalene-2-sulfonic acid, 3-nitrotyrosine, 3-dimethylamino phenol, p-aminobenzoic acid, and mixtures thereof.

10. A polymer of claim 9, wherein said polymer comprises aloin monomers.

11. A polymer of claim 9, wherein said polymer comprises dihydroxyphenylalanine monomers.

12. A polymer of claim 9, wherein said polymer comprises aloin monomers and dihydroxyphenylalanine monomers.

13. A polymer of claim 9, wherein said polymer further comprises a moiety selected from the group consisting of linoleic acid, 9,10-dihydroxystearic acid, linolenic acid, cholesterol, dihydroxycarbazole, and mixtures thereof.

14. A polymer of claim 9, wherein said polymer has a molecular weight of from about 10 kd to about 50 kd.

15. A polymer of claim 10, wherein said polymer has a molecular weight of from about 10 kd to about 50 kd.

16. A polymer of claim 12, wherein said polymer has a molecular weight of from about 10 kd to about 50 kd.

17. A composition comprising a polymer of claim 9 and cosmetically-acceptable topical carrier.

18. A method of darkening the skin, said method comprising applying to said skin a composition of claim 17.

\* \* \* \* \*

SEQUENCE LISTING

```
<160> NUMBER OF SEQ ID NOS: 30

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: C-terminal amidation
<220> FEATURE:
<221> NAME/KEY: MISC_FEATURE
<222> LOCATION: (4)..(4)
<223> OTHER INFORMATION: C-terminal Amidation

<400> SEQUENCE: 1

Leu Ile Gly Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: C-terminal Amidation

<400> SEQUENCE: 2

Leu Ile Gly Arg Leu
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (4)..(4)
<223> OTHER INFORMATION: C-terminal Amidation

<400> SEQUENCE: 3

Leu Ile Gly Lys
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: C-terminal Amidation

<400> SEQUENCE: 4

Ser Leu Ile Gly Lys
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Leu Ile Gly Arg
1

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

Leu Ile Gly Arg Leu
1               5

<210> SEQ ID NO 7
<211> LENGTH: 4
<212> TYPE: PRT
<213> ORGANISM: Artificial Sequence
<220> FEATURE:
<223> OTHER INFORMATION: Sythetetic Peptide

<400> SEQUENCE: 7

Leu Ile Gly Lys
1

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Ser Leu Ile Gly Lys
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 9

Leu Ile Gly Arg
1

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (5)..(5)
<223> OTHER INFORMATION: Amidated C-terminus

<400> SEQUENCE: 10

Leu Ile Gly Arg Leu
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 11

Leu Ile Gly Lys
1

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (5)..(5)
<223> OTHER INFORMATION: Amidated C-terminus

<400> SEQUENCE: 12
```

Ser Leu Ile Gly Lys
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 13

Leu Ile Gly Arg
1

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 14

Leu Ile Gly Arg Leu
1               5

<210> SEQ ID NO 15
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 15

Leu Ile Gly Lys
1

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 16

Ser Leu Ile Gly Lys
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE

```
<222> LOCATION: (1)..(1)
<223> OTHER INFORMATION: Stearatoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 17

Leu Ile Gly Arg
1

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (5)..(5)
<223> OTHER INFORMATION: Amidated C-terminus

<400> SEQUENCE: 18

Leu Ile Gly Arg Leu
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 19

Leu Ile Gly Lys
1

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (5)..(5)
<223> OTHER INFORMATION: Stearatoyl C-terminus

<400> SEQUENCE: 20

Ser Leu Ile Gly Lys
1               5

<210> SEQ ID NO 21
<211> LENGTH: 4
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus

<400> SEQUENCE: 21

Leu Ile Gly Arg
1

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus

<400> SEQUENCE: 22

Leu Ile Gly Arg Leu
1               5

<210> SEQ ID NO 23
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<222> LOCATION: (11)..(1)
<223> OTHER INFORMATION: Stearatoyl N-terminus

<400> SEQUENCE: 23

Leu Ile Gly Lys
1

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus

<400> SEQUENCE: 24

Ser Leu Ile Gly Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Amidated C-terminus

<400> SEQUENCE: 25

Ser Leu Ile Gly Arg Leu
1               5
```

```
<210> SEQ ID NO 26
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 26

Ser Leu Ile Gly Arg Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Amidated C-terminus
<220> FEATURE:
<221> NAME/KEY: MISC_FEATURE
<223> OTHER INFORMATION: Palmitoyl N-terminus

<400> SEQUENCE: 27

Ser Leu Ile Gly Arg Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Palmitoyl N-terminus

<400> SEQUENCE: 28

Ser Leu Ile Gly Arg Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Amidated C-terminus
<220> FEATURE:
<221> NAME/KEY: MISC_FEATURE
<223> OTHER INFORMATION: Stearatoyl N-terminus

<400> SEQUENCE: 29

Ser Leu Ile Gly Arg Leu
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<223> OTHER INFORMATION: Stearatoyl N-terminus

<400> SEQUENCE: 30

Ser Leu Ile Gly Arg Leu
1               5
```